(12) United States Patent
Scanlan et al.

(10) Patent No.: US 8,955,208 B1
(45) Date of Patent: Feb. 17, 2015

(54) INFORMATION HOLDER FOR MEDICAL INSTRUMENT STERILIZATION CONTAINERS

(75) Inventors: Timothy M. Scanlan, St. Paul, MN (US); Nancy L. Arnold, Andover, MN (US); Greg J. O'Donnell, Brook Park, MN (US)

(73) Assignee: Scanlan International, Inc., St. Paul, MN (US)

( * ) Notice: Subject to any disclaimer, the term of this patent is extended or adjusted under 35 U.S.C. 154(b) by 740 days.

(21) Appl. No.: 13/038,966

(22) Filed: Mar. 2, 2011

Related U.S. Application Data

(60) Provisional application No. 61/310,034, filed on Mar. 3, 2010.

(51) Int. Cl.
*B21D 39/00* (2006.01)
*A61B 19/02* (2006.01)

(52) U.S. Cl.
USPC .............................................. 29/428; 206/438

(58) Field of Classification Search
USPC ..................... 206/363, 438; 29/428
See application file for complete search history.

(56) References Cited

U.S. PATENT DOCUMENTS

| | | | |
|---|---|---|---|
| 3,754,700 A | 8/1973 | Bonk | |
| 4,149,329 A | 4/1979 | Graves | |
| 4,510,621 A * | 4/1985 | Sak et al. | 383/89 |
| 4,765,653 A * | 8/1988 | Fasham et al. | 462/84 |
| 4,820,499 A | 4/1989 | Taschner | |
| 4,844,259 A | 7/1989 | Glowczewskie, Jr. et al. | |
| 4,993,844 A | 2/1991 | Robinson et al. | |
| 5,098,676 A | 3/1992 | Brooks, Jr. | |
| 5,102,234 A | 4/1992 | Levy | |
| 5,372,787 A * | 12/1994 | Ritter | 422/119 |
| 6,073,767 A | 6/2000 | Cohen et al. | |
| 6,234,310 B1 * | 5/2001 | Goldhaber | 206/438 |
| 6,315,112 B1 * | 11/2001 | Garrill et al. | 206/204 |
| 6,343,695 B1 * | 2/2002 | Petrick et al. | 206/534 |
| 6,391,260 B1 | 5/2002 | Davis et al. | |
| 6,412,205 B1 | 7/2002 | Cheresko | |
| 6,517,916 B1 | 2/2003 | Bayer et al. | |
| 6,799,389 B2 | 10/2004 | Wolfgang | |
| 6,874,938 B2 | 4/2005 | Price et al. | |
| 6,880,869 B2 | 4/2005 | Schainholz et al. | |
| 7,341,148 B2 * | 3/2008 | Bettenhausen et al. | 206/370 |
| 7,560,082 B2 | 7/2009 | Stecklein et al. | |
| 2004/0111942 A1 | 6/2004 | Stonehocker | |
| 2006/0016708 A1 * | 1/2006 | Ingraham | 206/439 |
| 2007/0023309 A1 | 2/2007 | Davis | |
| 2007/0038200 A1 | 2/2007 | Hill | |
| 2008/0065043 A1 * | 3/2008 | Bemer | 604/408 |
| 2009/0272806 A1 | 11/2009 | Kemp et al. | |
| 2012/0000804 A1 | 1/2012 | Barnes et al. | |

FOREIGN PATENT DOCUMENTS

DE 29706115 U1 * 7/1997

\* cited by examiner

*Primary Examiner* — Jermie Cozart
(74) *Attorney, Agent, or Firm* — Vincent L. Pham

(57) ABSTRACT

An information holder for holding informational documents used to track and identify medical instruments can be releasably attached to a sterilization container or tray. The information holder includes an autoclavable material pouch and a releasable attachment structure coupled to the pouch for securing the information holder to sterilization container or tray. The attachment structure can include adhesive or a handle-engaging member. The information holder can be removed from the container or tray after sterilization without breaching the sterilization of the contents contained within sterilization container or tray. The information holder can be re-attached to the same or a different container.

16 Claims, 4 Drawing Sheets

INFORMATION HOLDER FOR MEDICAL INSTRUMENT STERILIZATION CONTAINERS

CROSS-REFERENCE TO RELATED APPLICATION

This application claims the benefit under 35 U.S.C. 119 of Provisional Application No. 61/310,034, filed Mar. 3, 2010, which is incorporated herein by reference in its entirety for all purposes.

TECHNICAL FIELD

The present invention relates to an information holder for medical instruments and/or medical instrument trays for tracking and identification purposes before and after sterilization.

BACKGROUND OF THE INVENTION

The tracking and identification of surgical instruments and/or surgical devices after they have been cleaned and sterilized for use in the operating environment is difficult. After devices have been cleaned they are placed into rigid sterilization containers or are placed in sterilization baskets/trays and are then wrapped with sterilization paper. The rigid containers cannot be opened and the sterilization paper cannot be removed as sterility will be compromised. Thus, identification of these devices in the rigid containers or sterilization trays cannot be done by visually inspecting them. The number and identification of these devices is generally accomplished through manual record keeping. Hospital staff will record the contents of the sterilization tray on an informational document, some of which are commonly referred to as a "Count Sheet", and will place this informational document or multiple informational documents into the rigid sterilization container or in a sterilization tray/basket, which is then wrapped with sterilization paper. The difficulty with this methodology is that the informational document(s) placed into the sterilization tray may compromise or otherwise create an issue with the sterilization of the devices inside the sterilization tray.

SUMMARY OF THE INVENTION

One embodiment of the invention is a holder or container for surgical instrument informational documents that can be releasably attached to a sterilization tray or container. One embodiment of the holder includes a polymer pouch. In another embodiment of the invention, the pouch substantially encloses the informational documents. Other embodiments of the invention have adhesive with a release liner or another attachment structure on the holder for attaching the holder to the tray. In another embodiment, the releasable attachment structure includes a handle-engaging member such as a looped member, a strap, or a releasable cable tie.

Figure 1A:
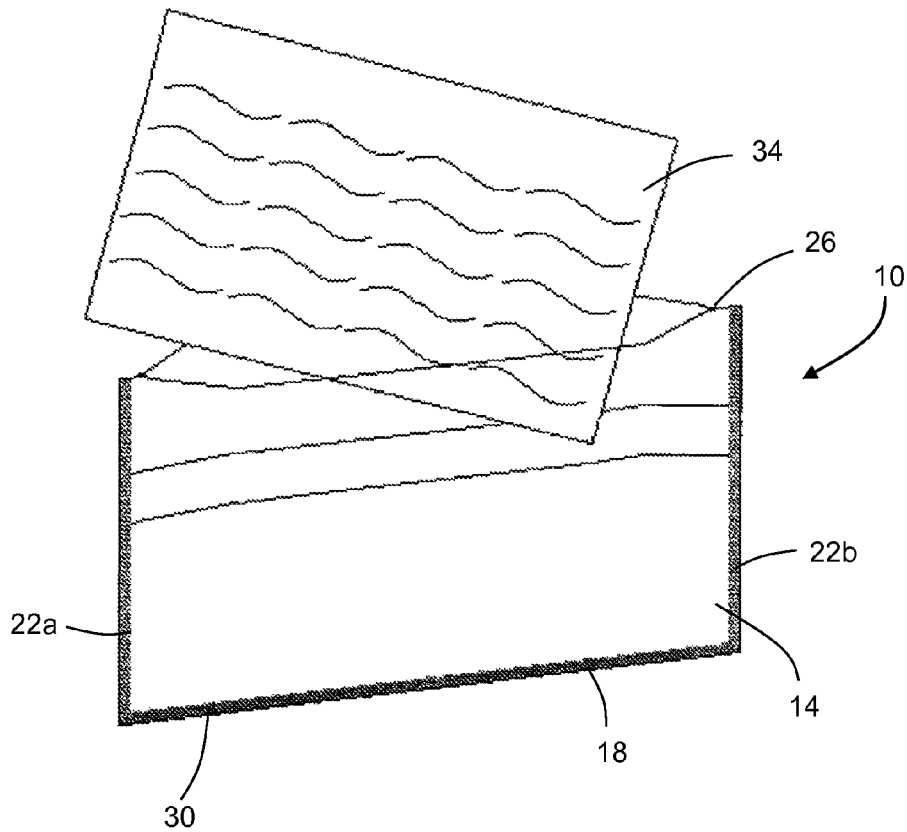
FIGS. 1A and 1B are front and back schematic views of an information holder in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The invention is an information holder that has a number of important features. The information holder can hold the informational document(s) in a manner that will not impede sterilization of the surgical instrument/surgical devices within the sterilization container or tray. The holder facilitates easy removal and review of the informational document(s) without compromising the sterility of the surgical instrument/surgical devices within the sterilization container or tray. The holder also can be quickly and easily attached and removed if needed from the outside of the sterilization container or tray. Additionally, the information holder, according to the various embodiments as described herein, provides a rapid method for the hospital staff to hold and attach the informational document(s) without the worry of impeding sterilization, and that facilitates a quick review of the informational document(s) without needing to open the tray, which may possibly breach sterilization.

Figure 1B:
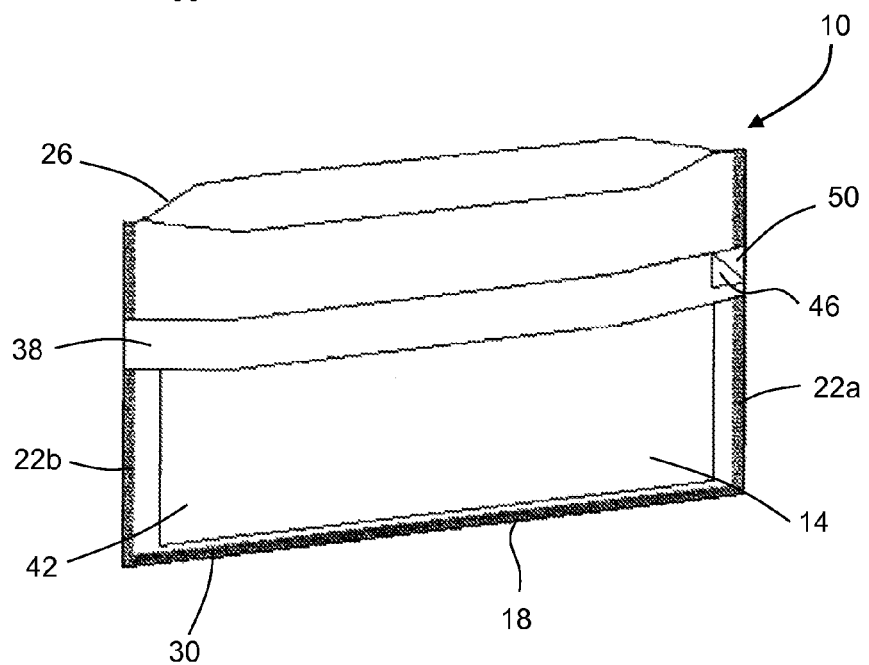

FIGS. 1A and 1B are front and back views of an information holder 10 according to one embodiment of the invention. As shown in FIGS. 1A and 1B, one embodiment of the information holder 10 includes transparent, autoclavable polymer material 14, which can, but need not be, biodegradable, and that is manufactured into the shape of a pouch 30, sealed at the bottom 18 and both sides 22a, 22b, and open at the top 26, thus forming a bag or pouch or other container to hold and preferably substantially enclose the informational document(s) 34. One example of an informational document that can be enclosed in the pouch 30 is a count sheet for recording the contents of a sterilization container or tray.

Double sided tape 38, made of a polymer carrier, a polymer release liner, and adhesive on both sides, can be adhered to the back side 42 of the pouch 30. A release liner 46 remains on the adhesive 50 on the side of the double sided tape 38 that is not adhered to the pouch 30. The pouch 30 is preferably large enough to hold multiple informational documents 34 securely. In other embodiments, other releasable structures, such as clips attached to the pouch, can be used to releasably attach the pouch to the instrument tray.

Figure 1C:
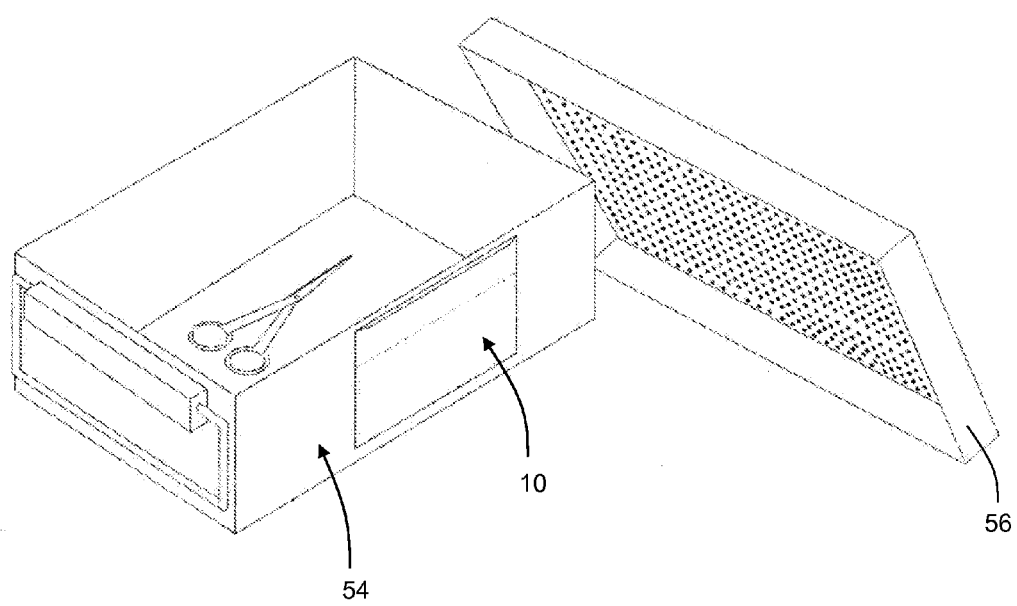
FIG. 1C is a schematic view showing the information holder of FIGS. 1A and 1B in use.

FIG. 1C shows the information holder 10 in use with a sterilization tray 54 including an optional lid 56. In use, according to one embodiment, the user can fold the informational document(s) 34 and place them into the information holder 10. The user removes the release liner (not shown) and attaches the information holder 10 to the sterilization tray 54 via the adhesive strip on the backside of the information holder 10 (or otherwise attaches the holder 10 to the tray 54). The sterilization tray 54 with the information holder 10 is then placed into the sterilizer. When removed from the sterilizer, the user may remove and view the informational document(s) 34 without fear of breaching sterilization and can place the informational document(s) back into the information holder 10 to maintain identification of the items in the sterilization tray 54.

The information holder 10 can be removed and reused. The information holder 10 can remain on the sterilization tray for additional use or may be removed by simply grabbing onto the information holder 10 and pulling it off of the sterilization tray 54. For example, as described above according to one embodiment, the adhesive holding the information holder 10 to the sterilization tray 54 will release when the information holder 10 is pulled away from the tray 54. The information holder 10 can then be placed onto another sterilization tray.

Figure 2A:
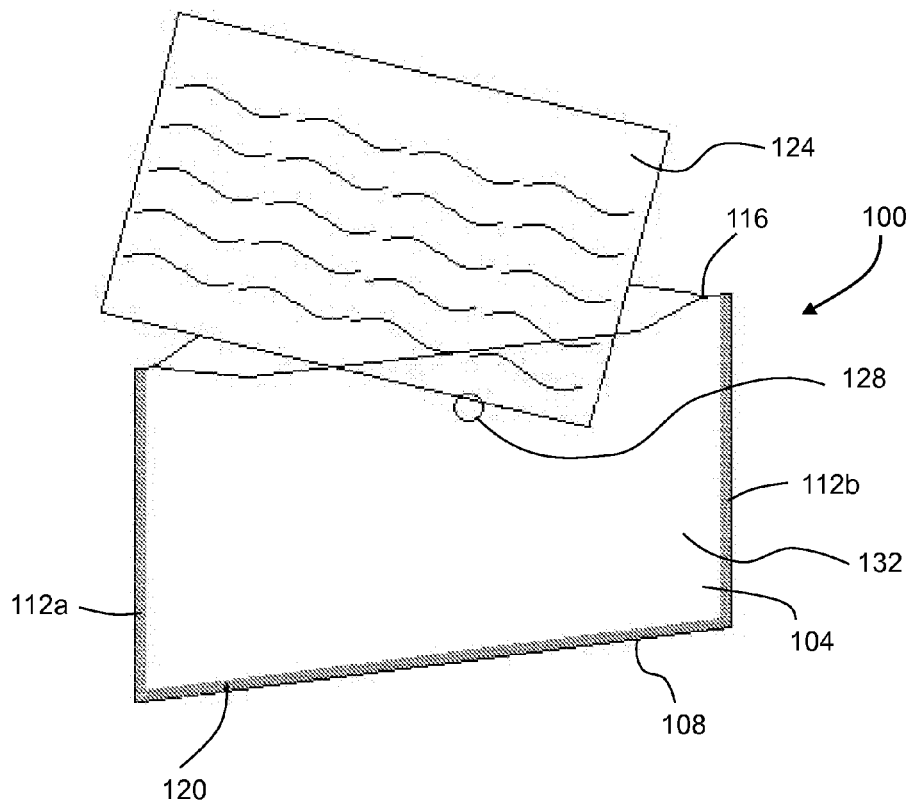
FIGS. 2A and 2B are front and back schematic views of an information holder in accordance with another embodiment of the present invention.
Figure 2B:
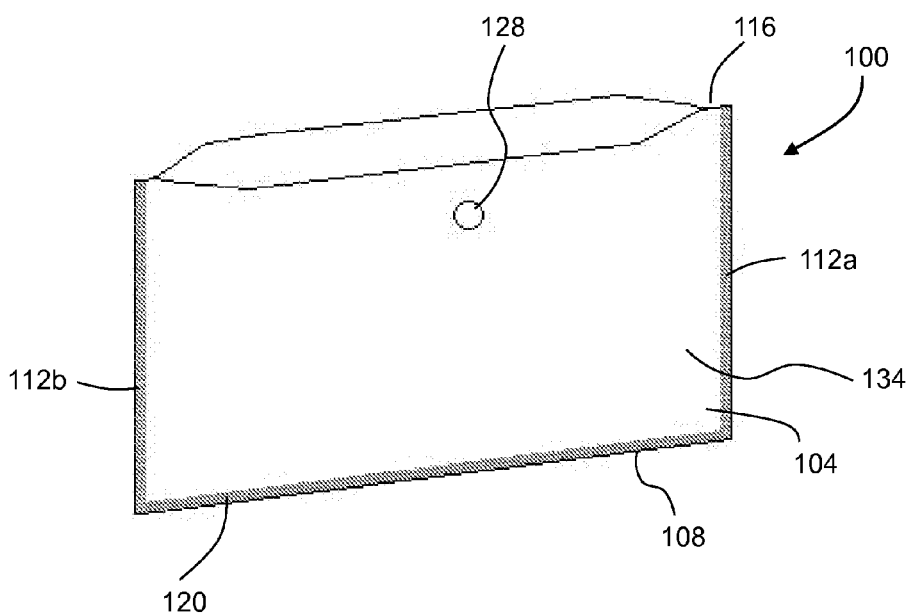
Figure 2C:
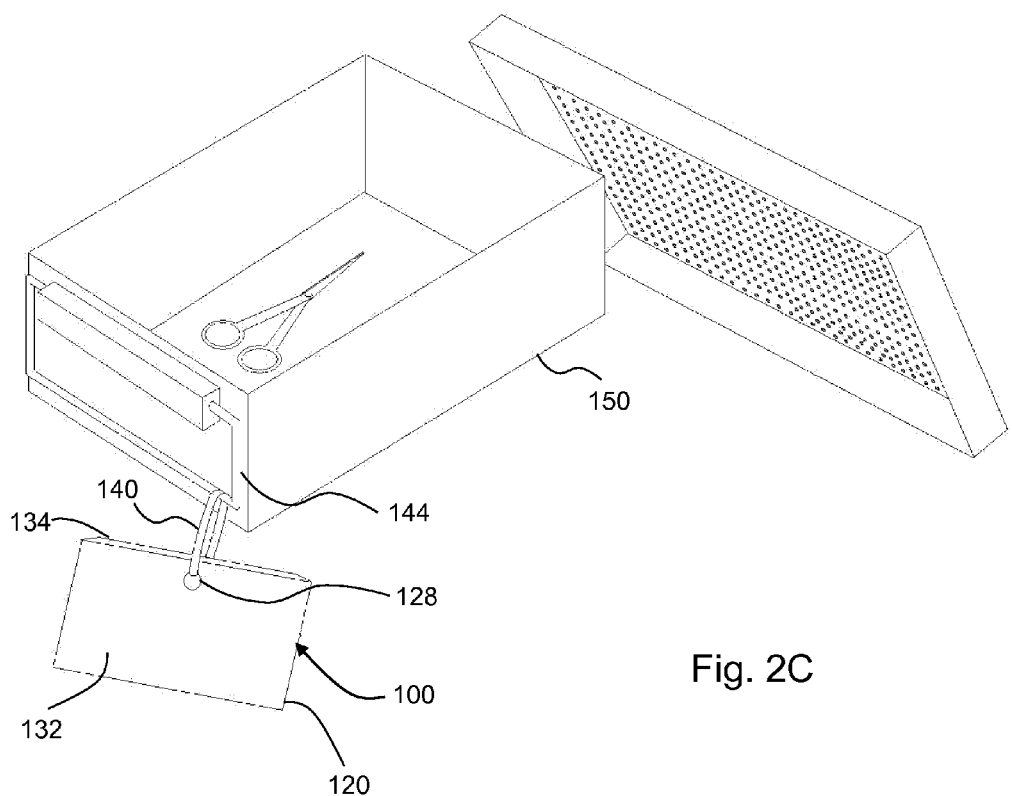
FIG. 2C is a schematic view showing the information holder of FIGS. 2A and 2B in use.

FIGS. 2A and 2B are front and back views of an information holder 100 according to another embodiment of the present invention. Like the information holder 10, described above with reference to FIGS. 1A-1C, the information holder 100 is configured for releasable attachment to a sterilization tray (FIG. 2C). The information holder 100 includes transparent, autoclavable polymer material 104, which can, but need not be, biodegradable, and that is manufactured into the shape of a pouch, sealed at the bottom 108 and both sides 112a, 112b, open at the top 116, thus forming a bag or pouch 120 or other container to hold and preferably substantially enclose the informational document(s) 124. According to various embodiments, the pouch 120 is large enough to hold multiple informational documents 124 securely. One example of an informational document 124 that can be enclosed in the pouch 120 is a count sheet.

Additionally, as shown in FIGS. 2A and 2B, the information holder 100 includes at least one aperture 128 formed in both the front 132 and back 134 of the pouch 120. In one embodiment, the aperture 128 formed in the front 132 of the pouch 120 is superimposed over the aperture 128 formed in the back 134 of the pouch 120. According to some embodiments, the apertures 128 can be die cut holes or slits formed in the front 132 and/or back 134 of the pouch.

As shown in FIG. 2C, the information holder 100 also includes a handle-engaging member 140, such as, for example, a cable tie, strap, looped member or other similar attachment means for attaching the information holder to the sterilization tray 150. The handle-engaging member 140 is looped through the apertures 128 provided in the front 132 and back 134 of the pouch 120 and around a handle 144 of the sterilization tray 150 to attach the information holder 100 to the sterilization tray 150. In preferred embodiments of the invention the member 140 is configured as a releasable member (e.g., it can have a buckle or can be broken by physical force). In other embodiments of the invention the handle-engaging member 140 is attached to pouch 120 by other approaches (e.g., is adhesively attached to the pouch).

Referring to FIG. 2C, which shows the information holder 100 in use, the user can fold the informational document(s) and place them into the information holder 100. The user inserts the handle-engaging member 140 through the apertures 128 provided in the front 132 and back 134 of the pouch 120 and loops the handle-engaging member 140 around the handle 144 of the sterilization tray 150, securing the handle-engaging member 140 to the sterilization tray 150. The sterilization tray 150 with the information holder 100 including the information document(s) enclosed therein is then placed into the sterilizer. When removed from the sterilizer, the user may remove and view the informational document(s) without fear of breaching sterilization and can place the informational document(s) back into the information holder 100 to maintain identification of the items contained in the sterilization tray 124. The information holder 100 can remain on the sterilization tray 150 for additional use or the information holder 100 can be removed and reused by attaching the information holder 100 to another sterilization tray.

In other embodiments, the information holder, as described herein, is opaque. In still other embodiments, the information holder can be manufactured with various clear or colored polymers for immediate visual identification. Different colors may be used to identify different types of surgical procedures, surgeon owned instruments, configurations, locations, etc. Clear information holders allow for inspection of the informational documents within. Materials other than polymers can also be used for the pouch.

The sterilization environment for surgical instrument/surgical devices is severe involving heat, moisture, chemicals and gases or any combination thereof. The information holders' polymers or other components and adhesives are stable in this environment.

As an example, one embodiment of the invention includes a pouch formed from high density polypropylene (HDPE). A carrier formed from material such as polyethylene terephthalate (PTE) is attached to the pouch by a permanent acrylic adhesive. A removable acrylic adhesive that is used to releasably secure the pouch (and carrier) to the sterilization tray is applied to the side of the carrier opposite the permanent adhesive. A liner of material such as low density polyethylene (LDPE) can be applied over the removable adhesive to protect the carrier and adhesives prior to use of the information carrier. When the liner is removed the information carrier can be attached to the sterilization container.

Although the invention is described and shown in connection with the embodiments described herein, those skilled in the art will recognize that changes can be made in form and detail without departing from the spirit and scope of the invention.

What is claimed is:

1. A method for identifying devices in a sterilization container or tray comprising:
    inserting an informational document into an autoclavable material pouch;
    placing a device into the sterilization container or tray;
    attaching the pouch to an outside of the sterilization container or tray, wherein attaching the pouch includes manipulating an attachment structure; and
    sterilizing the sterilization container or tray with a device inside of and a pouch on the outside of the sterilization container or tray.

2. The method of claim 1, wherein attaching the pouch includes releasably attaching the pouch to the container or tray.

3. The method of claim 2, further including removing the pouch from the sterilization container or tray.

4. The method of claim 3, further comprising re-attaching the pouch to the container or tray.

5. The method of claim 1, wherein attaching the pouch to the sterilization container or tray includes adhesively attaching the pouch to the container or tray.

6. The method of claim 5 wherein manipulating the attachment structure includes removing a release liner from the attachment structure, the attachment structure being an adhesive attachment structure.

7. The method of claim 1 wherein attaching the pouch to the sterilization container or tray includes attaching the pouch to a generally planar surface of the outside of the sterilization container or tray.

8. The method of claim 1 further including reviewing the informational document without compromising the sterility of the devices in the sterilization container or tray.

9. The method of claim 8 wherein reviewing the document includes removing the informational document from the pouch.

10. The method of claim 9 further comprising reinserting the informational document after review without compromising the sterility of the devices in the sterilization container or tray.

11. The method of claim 1 wherein the device placed into the sterilization container or tray is a sterilizable device.

12. The method of claim 1 wherein the informational document is a count sheet.

13. The method of claim 1 wherein the informational document is folded.

14. The method of claim 1 further comprising manipulating the sterilization container or tray to close the a sterilization container or tray, wherein the pouch is placed on the outside of the closed container or tray.

15. A method for identifying devices in a sterilization container or tray comprising:
   inserting an informational document into an autoclavable material pouch; and.
   placing a device into the sterilization container or tray;
   attaching the pouch to an outside of the sterilization container or tray, wherein attaching the pouch includes manipulating an attachment structure; and
   manipulating the sterilization container or tray to substantially enclose the device inside, wherein manipulating the sterilization container or tray includes wrapping the sterilization tray in sterilization paper, wherein the pouch is placed on the outside of the wrapping.

16. The method of claim 15 wherein manipulating the sterilization container or tray includes closing a sterilization container or tray, wherein the pouch is placed on the outside of the closed container or tray.

* * * * *

UNITED STATES PATENT AND TRADEMARK OFFICE
CERTIFICATE OF CORRECTION

PATENT NO. : 8,955,208 B1
APPLICATION NO. : 13/038966
DATED : February 17, 2015
INVENTOR(S) : Timothy M. Scanlan et al.

Page 1 of 1

It is certified that error appears in the above-identified patent and that said Letters Patent is hereby corrected as shown below:

In the Claims

In Claim 15, Column 6, Line 4, delete "and."

Signed and Sealed this
Ninth Day of June, 2015

Michelle K. Lee
*Director of the United States Patent and Trademark Office*